United States Patent
Alt

(10) Patent No.: US 12,362,054 B2
(45) Date of Patent: Jul. 15, 2025

(54) MONITORING SYSTEM AND METHOD

(71) Applicant: Sanofi, Paris (FR)

(72) Inventor: Stefan Alt, Frankfurt am Main (DE)

(73) Assignee: Sanofi, Paris (FR)

( * ) Notice: Subject to any disclaimer, the term of this patent is extended or adjusted under 35 U.S.C. 154(b) by 588 days.

(21) Appl. No.: 17/641,190

(22) PCT Filed: Sep. 7, 2020

(86) PCT No.: PCT/EP2020/074894
§ 371 (c)(1),
(2) Date: Mar. 8, 2022

(87) PCT Pub. No.: WO2021/048035
PCT Pub. Date: Mar. 18, 2021

(65) Prior Publication Data
US 2022/0351821 A1    Nov. 3, 2022

(30) Foreign Application Priority Data

Sep. 10, 2019   (EP) ..................... 19306085

(51) Int. Cl.
*G16H 20/17*    (2018.01)
*H04L 9/08*     (2006.01)

(52) U.S. Cl.
CPC ............. *G16H 20/17* (2018.01); *H04L 9/088* (2013.01)

(58) Field of Classification Search
None
See application file for complete search history.

(56) References Cited

U.S. PATENT DOCUMENTS

| | | | | |
|---|---|---|---|---|
| 9,022,988 | B1 * | 5/2015 | Shaban | A61M 5/1456 604/189 |
| 2016/0012205 | A1 * | 1/2016 | Saint | H04B 7/24 604/189 |
| 2018/0369514 | A1 * | 12/2018 | Adelson | A61M 15/008 |
| 2019/0036914 | A1 * | 1/2019 | Tzur-David | H04L 9/0861 |
| 2019/0156938 | A1 * | 5/2019 | Brunner | G16H 10/60 |

(Continued)

FOREIGN PATENT DOCUMENTS

| CN | 105264565 A | 1/2016 |
|---|---|---|
| CN | 106687961 A | 5/2017 |

(Continued)

OTHER PUBLICATIONS

Jia et al. ("Intelligent and privacy-preserving medication adherence system." Smart Health 9 (2018): 250-264) (Year: 2018).*

(Continued)

*Primary Examiner* — Christopher B Tokarczyk
(74) *Attorney, Agent, or Firm* — Fish & Richardson P.C.

(57) ABSTRACT

A monitoring system comprises a first device comprising a computer code that when executed by the first device causes the first device to: receive a first security code unique to a second device, the first security code retrieved from a label provided in association with the second device; receive a packet broadcast by the second device, the packet having a second security code unique to the second device and an encrypted payload including a dose record; generate a cryptographic key unique to the second device, based on the first security code and the second security code; and store the cryptographic key.

20 Claims, 8 Drawing Sheets

(56) References Cited

U.S. PATENT DOCUMENTS

| | | | |
|---|---|---|---|
| 2019/0198144 A1* | 6/2019 | Blackley | G16H 50/20 |
| 2019/0217022 A1 | 7/2019 | Gentz et al. | |
| 2020/0135321 A1* | 4/2020 | Lebrun | G06F 21/33 |

FOREIGN PATENT DOCUMENTS

| | | |
|---|---|---|
| CN | 108028755 A | 5/2018 |
| JP | 2005-295408 A | 10/2005 |
| JP | 2017-504873 A | 2/2017 |
| JP | 2017-524427 A | 8/2017 |
| WO | WO 2011/117212 | 9/2011 |
| WO | WO 2014/197774 | 12/2014 |
| WO | WO 2015/082578 A1 | 6/2015 |
| WO | WO 2015/197749 | 12/2015 |
| WO | WO 2016/131713 | 8/2016 |
| WO | WO 2016/142511 | 9/2016 |
| WO | WO 2016/198616 | 12/2016 |
| WO | WO 2017/005961 | 1/2017 |

OTHER PUBLICATIONS

International Preliminary Report on Patentability in International Appln. No. PCT/EP2020/074894, dated Mar. 24, 2022, 8 pages.
International Search Report and Written Opinion in International Appln. No. PCT/EP2020/074894, dated Nov. 13, 2020, 9 pages.

* cited by examiner

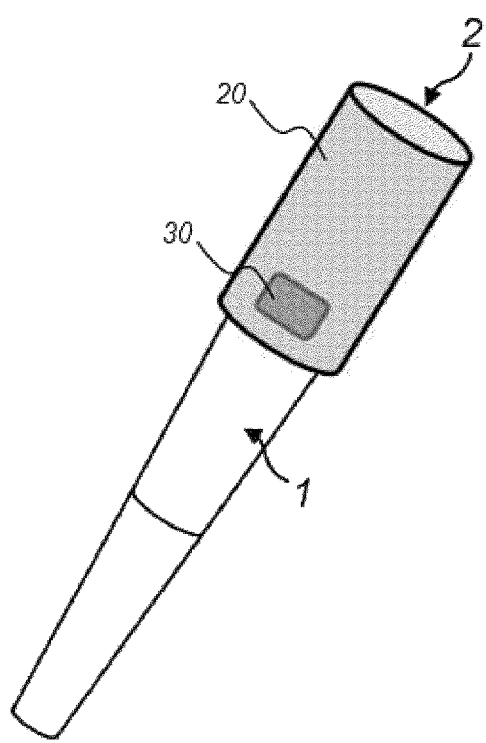 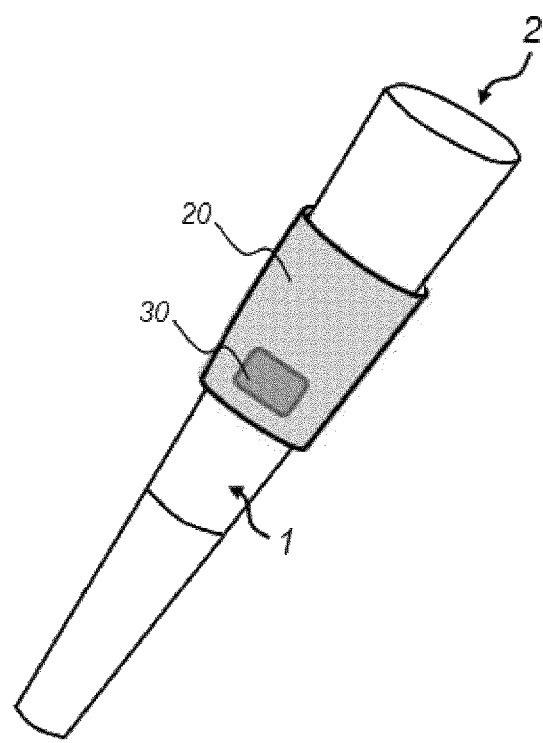
FIG. 2AFIG. 2B

MONITORING SYSTEM AND METHOD

CROSS REFERENCE TO RELATED APPLICATIONS

The present application is the national stage entry of International Patent Application No. PCT/EP2020/074894, filed on Sep. 7, 2020, and claims priority to Application No. EP 19306085.2, filed on Sep. 10, 2019, the disclosures of which are incorporated herein by reference.

TECHNICAL FIELD

The present disclosure relates to a monitoring system including a first device and a second device and to a method of operating the monitoring system.

BACKGROUND

A variety of diseases exist that require regular treatment by injection of a medicament. Such injections can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage dial and observing the actual dose from a dosage window of the insulin pen. The dose is then injected by inserting the needle into a suited skin portion and pressing an injection button of the insulin pen. To be able to monitor insulin injection, for instance to prevent false handling of the insulin pen or to keep track of the doses already applied or remaining, it is desirable to measure information related to a condition and/or use of the injection device, such as information on the injected insulin type and dose.

For a good treatment of insulin it is necessary to keep a diary to document the day, time and amount of insulin dose. Some patients forget to write the information down or cannot remember when and how much insulin they have injected. Therefore, there is a strong need for further support or automation of this process to make it easier for the patient to keep track of their diary.

It has been described, for instance, in WO 2011/117212 to provide a supplementary device comprising a mating unit for releasably attaching the device to an injection device. The device includes a camera and is configured to perform optical character recognition on captured images visible through a dosage window of the injection pen, thereby to determine a dose of medicament that has been dialled into the injection device.

It has also been described, for instance in, WO 2015/197749 to provide a monitoring system comprising a first device configured to capture an image of a medicament dosage indicated by a medicament dispensing device and transmit data representing the image of the medicament dosage to a second device. The second device configured to receive and perform optical character recognition on the data to identify the dosage indicated by the medicament dispensing device and make a non-transient record of dosage information based at least in part on the identified medicament dosage.

The medication dose history of a patient is a form of medical information and thus is also regarded as private or confidential in nature. It is therefore important that any process for recording, transferring and storing the individual administered dose records and/or the overall medication dose history of the patient is carried out safely and securely to protect the patient's private medical information.

SUMMARY

According to a first aspect of the present disclosure, there is provided a first device comprising a computer code that when executed by the first device causes the first device to receive a first security code unique to a second device, the first security code retrieved from a label provided in association with the second device; receive a packet broadcast by the second device, the packet having a second security code unique to the second device and an encrypted payload including a dose record; generate a cryptographic key unique to the second device, based on the first security code and the second security code; and store the cryptographic key.

The provision of a label is advantageous as it requires the first device and the second device or user to be physically proximal to each other to obtain the first security code that is used to enable the first device and the second device to sync with each other. In turn, this reduces the likelihood of other, potentially malicious devices synchronising with the second device or intercepting transmitted payloads, thereby increasing the security of the user's medication dose history.

The provision of a label also improves security as the label only provides one factor of a two-factor authentication system that enables the payload to be decrypted.

The provision of a label having a first security code allows any device that has scanned the label to decrypt the data packets. This is advantageous should it be necessary to employ multiple first devices, such as a tablet and a smart phone, to keep a record of a patient's medication dose history.

Alternatively, the fact that the label may be removed and disposed of minimises the opportunity for malicious devices to gain physical access to the label, determine the first security code and try to intercept encrypted payloads.

The first device may also decrypt the encrypted payload using the cryptographic key to produce a decrypted dose record and store the decrypted dose record in a memory.

The provision of a cryptographic key is advantageous as, contrary to default Bluetooth pairing/bonding or custom (application layer) pairing where a new random key is generated and shared, the second device is never bound to one single first device or user, as the encryption key is fixed to the second device.

The provision of the cryptographic key also enables symmetric encryption at both the first device and the mobile device of any payload to be transmitted between the first and second devices. Advantageously, this enables the transfer of dose records to occur more securely as the process of data encryption is independent of the exact contents of the payload itself. The system also allows for minimal interaction from a user, as once the first device has stored the unique cryptographic key, the first device is able to receive subsequent payloads automatically and more securely, without the need to pair to the second device over an open network.

The first device may also, when the dose record is decrypted, determine whether previous dose records are missing from the memory; and when it is determined that at least one previous dose record is missing from the memory, send a connection request to the second device; receive from the second device a dose record packet having an encrypted payload including the at least one missing previous dose record; decrypt the encrypted payload of the dose record packet using the cryptographic key; and store the at least one missing previous dose record in the memory.

The first device may also, when the dose record is decrypted, determine whether previous dose records are missing from the memory; and when it is determined that no previous dose records are missing from the memory, provide no response to the second device.

This is advantageous as it ensures that the first device is still able to maintain a complete medication dose history for a patient without having to receive a dose record after each medicament delivery event. Instead, the first device ensures that records are updated whenever in proximity to the second device. The fact that this update occurs in response to a connection request ensures greater energy efficiency at both the first device and the second device.

The cryptographic key may be an initial cryptographic key, and the first device may, after the initial cryptographic key is generated, transmit a new cryptographic key to the second device, where the new cryptographic key is encrypted using the initial cryptographic key.

This is advantageous as, in the event that a malicious device has gained access to the cryptographic key of the second device prior, the malicious device will not be able to determine the new cryptographic key provided by the first device, thereby increasing the security of the user's medication dose history. This is also done with minimal input by the user.

The first device may generate the cryptographic key using at least one hash function in combination with the first security code and second security code.

This is advantageous as the use of a hash function can be readily and efficiently implemented on the first device and adds an extra layer of security. As it can be done efficiently it can also minimise processing power.

The first device may be provided as a mobile device capable of wireless communication.

This is advantageous as such mobile devices are readily available to and well known by the majority of users and therefore easy to use and implement.

According to a second aspect of the present disclosure, there is provided a second device for recording information concerning the use of a medicament delivery device, the second device comprising a transmitter configured to wirelessly broadcast data; a memory configured to store a cryptographic key unique to the second device and a plurality of dose records; and a processor configured to control the transmitter to broadcast a packet having a second security code unique to the second device and an encrypted dose record encrypted using the stored cryptographic key. The second security code is one factor of a two-factor authentication system for allowing generation of the cryptographic key.

The use of BLE broadcasting is advantageous as it reduces the need for BLE connections and thereby improves the energy efficiency of the second device. It is also possible to use BLE broadcasting in association with a variety of platforms, such as android and iOS platforms.

The second device may, before the packet is broadcast, detect a user input indicating that an injection process of the medicament delivery device is complete; capture information representing a dosage dialled or delivered at the medicament delivery device; generate a dose record from the captured information; generate an encrypted payload including the dose record using the cryptographic key; and broadcast a packet having the second security code and the encrypted payload.

This configuration is advantageous as it can be done efficiently whilst minimising power consumption. It also improves security as the packet only provides one factor of a two-factor authentication system that enables the payload to be decrypted.

The second device may receive a connection request from a first device, the connection request requesting a missing dose record; and in response to receiving the connection request, control the transmitter to transmit the missing dose record to the apparatus.

The process of transmitting encrypted packets in response to a connection request is advantageous as it reduces unwanted traceability of encrypted payloads, it reduces energy consumption of the second device and it allows multiple use events of a medicament delivery device. It also ensures that the first device can keep an updated and complete medication dose history. This is advantageous as the first device does not require the Internet or the provision of a cloud service to retain a complete medication dose history.

The cryptographic key may be an initial cryptographic key, and the second device may be configured to receive from the first device a new cryptographic key encrypted by the initial cryptographic key and to store the new cryptographic key.

The provision of a new cryptographic key is advantageous as it results in 1-to-1 binding between the first and second devices, thereby hindering re-pairing with malicious devices. It also ensures that the first security code provided by the label is only valid on first use. This can hinder easy re-pairing, thereby preventing malicious devices with (temporary) physical access to the label from using the first security code to try and intercept encrypted payloads.

The second device may be configured to store the cryptographic key and the second security key in a volatile memory; and delete the cryptographic key and the second security key prior to depletion of a battery of the second device.

It is advantageous to delete the cryptographic key and the second security key just before the battery of the second device is depleted, as it ensures that dose records in the medication dose history cannot be decrypted any more by a malicious device accessing the memory of the second device.

The second device may be a supplemental device provided with a part for coupling the supplemental device to the medicament delivery device. Alternatively, the second device may be an integral part of the medicament delivery device.

The dose record may also include a time and/or date and/or dose sequence identifier.

In combination, the first and second devices provide a more secure, two-factor authentication system, requiring the use of a first security code that is not stored in the memory of the second device, in combination with a second security code that is stored in the memory of the second device. This improves the security of the patient's medication dose history as it at least requires any attacker to gain physical access to the medical delivery device or monitor and record broadcast traffic. It also ensures that dose records are always encrypted and cannot be easily intercepted by malicious software applications on the first device.

According to third aspect of the present disclosure there is provided a method of operating a monitoring system including a first device and a second device, the method comprising: at the first device: receiving a first security code unique to the second device, the first security code retrieved from a label provided in association with the second device; receiving a packet broadcast by the second device, the packet having a second security code unique to the second device and an encrypted payload including a dose record; generating a cryptographic key unique to the second device, based on the first security code and the second security code; and storing the cryptographic key.

The method may also include, at the second device, prior to broadcasting the packet, detecting a user input indicating that an injection process of a medicament delivery device is complete; capturing an image of a dosage dialled at the medicament delivery device representing a dose record; generating an encrypted payload including the dose record using the cryptographic key of the second device; generating a packet having the second security code and the encrypted payload; and broadcasting the packet.

The method may also include, at the first device decrypting the encrypted payload using the cryptographic key to produce a decrypted dose record; and storing the decrypted dose record. The method may also include, at the first device: in response to providing the decrypted dose record, determining whether previous dose records are missing from the memory; and if it is determined that at least one previous dose record is missing from the memory, sending a connection request to the second device; receiving from the second device a dose record packet having an encrypted payload including the at least one missing previous dose record; decrypting the encrypted payload of the dose record packet using the cryptographic key; and storing the at least one missing previous dose record in the memory.

The connection request may include at least an encrypted command requesting connection to the second device and receipt of the missing dose records in the form of a dose record packet, and the connection request may be encrypted using the cryptographic key specific to the second device.

The method may also include, at the second device establishing a connection with the first device via an open BLE connection; and transmitting a dose record packet including the at least one missing previous dose record.

This method is advantageous as it only rarely requires BLE connections in response to connection request. Otherwise, BLE broadcasting is used. This improves the energy efficiency of the devices.

The method may also include, at the first device in response to providing the decrypted dose record, determining whether previous dose records are missing from the memory; and if it is determined that no previous dose records are missing from the memory, providing no response to the second device.

The cryptographic key may be an initial cryptographic key, and the method may also include, after generating the initial cryptographic key at the first device, transmitting by the first device a new cryptographic key encrypted by the initial cryptographic key to the second device.

The method may also include, at the second device storing the cryptographic key and the second security key in a volatile memory; and deleting the cryptographic key and second security key immediately prior to depletion of a battery of the second device.

The method may also include generating the cryptographic key using at least one hash function.

The first security code may be a key seed code. The second security code may be a salt code.

The label may be in the form of a sticker having a Quick Response code. The use of a Quick Response code is advantageous as it is provides a versatile means by which most types of data can be encoded and the information can be read by a variety of different devices with scanning capabilities.

The label or the advertising packet may also include an identification number unique to the second device.

The use of a long digitally transmitted second security code and the first security code with the option to include an identification number is advantageous as it provides a good cryptographic strength for encryption.

According to a fourth aspect of the present disclosure, there is provided a monitoring system comprising a first device according to the first aspect of the present disclosure and a second device according to the second aspect of the present disclosure.

According to a fifth aspect of the present disclosure, there is provided a computer program comprising machine readable instructions that when executed by a processing arrangement, causes the processing arrangement to perform a method according to the third aspect of the present disclosure.

According to a sixth aspect of the present disclosure, there is provided smartphone app comprising a computer program according to the fifth aspect of the present disclosure.

The provision of a discrete software module that is distinct from other software modules of the first device is advantageous as it may be provided in the first device on manufacture or it may be downloaded into the first device by a user, for instance from an application market place or application store.

Various other advantages will be apparent to the skilled person in relation to the embodiments of the present disclosure.

Embodiments of the disclosure will now be described, by way of example only, with reference to the accompanying drawings.

BRIEF DESCRIPTION OF THE FIGURES

In the Figures:

FIG. 2 is schematic view of an exemplary sensor device or supplementary device attached to a drug delivery device, according to embodiments of the present disclosure. FIGS. 2A and 2B show examples of how the supplementary device may be attached to the drug delivery device at a variety locations or positions;

FIG. 4 shows a mobile device wirelessly communicating with an apparatus according to embodiments of the present disclosure.

DETAILED DESCRIPTION

In the following, embodiments of the present disclosure will be described with reference to a disposable insulin injection device. The present disclosure is however not limited to such application and may equally well be deployed with injection devices that eject other medicaments or with other types of medicament administration devices. The present disclosure is also not limited to a disposable injection device and may equally well be employed with a re-usable injection device.

In the following, embodiments of the present disclosure will also be described with reference to a mobile device. The mobile device represents an exemplary first device of the present disclosure. The present disclosure is not, however, limited to such application and the first device may equally well be a processor, a controller, a circuit on a chip, an ASIC, or other similarly suitable examples.

Figure 1:
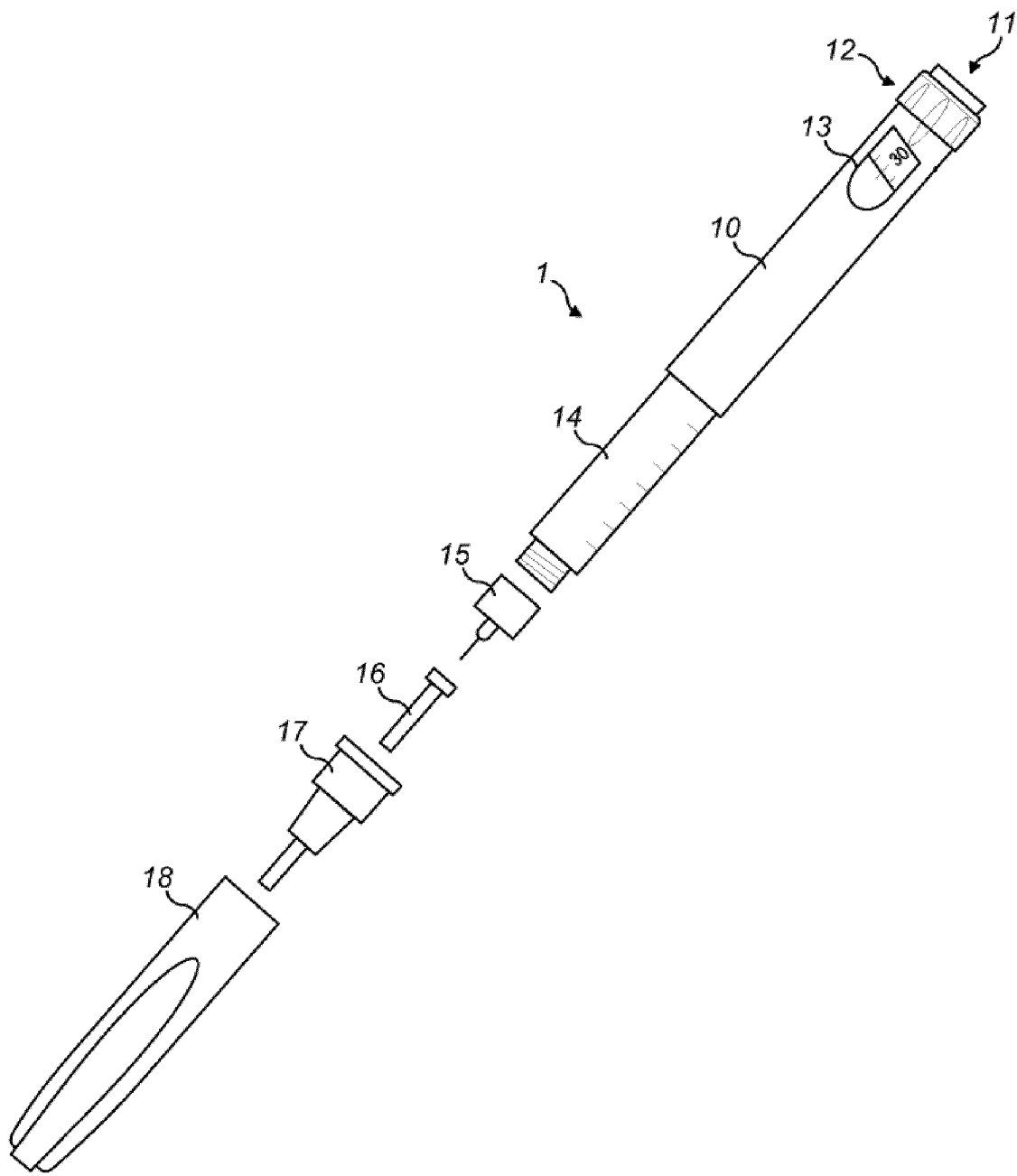
FIG. 1 is an exploded view of a drug delivery device.

FIG. 1 is an exploded view of an injection device 1, which may for instance represent Sanofi's Solostar™ insulin injection pen.

The injection device 1 of FIG. 1 is a pre-filled, disposable injection pen that comprises a housing 10 and contains an insulin container 14 to which a needle 15 can be affixed. The needle 15 is protected by an inner needle cap 16 and an outer needle cap 17, which in turn can be covered by a cap 18. An insulin dose to be ejected from the injection device 1 can be selected by turning the dosage dial 12. The selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may, for instance, be 30 IUs, as shown in FIG. 1. It should be noted that the selected dose may equally well be displayed differently, for instance, by means of an electronic display.

Turning the dosage dial 12 causes a mechanical clicker to provide haptic and acoustic feedback to a user. The numbers displayed in dosage window 13 are present on a sleeve by printing and the sleeve is contained in housing 10 and mechanically interacts with a piston in insulin container 14. When needle 15 is stuck into a skin portion of a patient and then injection button 11 is pushed, the insulin dose displayed in dosage window 13 will be ejected from the injection device 1. When the needle 15 of the injection device 1 remains for a certain time in the skin portion after the injection button 11 is pushed, a high percentage of the dose is actually injected into the patient's body. Ejection of the insulin dose also causes a mechanical click sound, which is different from the sounds produced when using dosage dial 12.

The injection device 1 may be used for several injection processes until either insulin container 14 is empty or the expiration date of the injection device 1 is reached (e.g. 28 days after the first use).

The injection device 1 also comprises an apparatus 2 configured to record information concerning the use of the injection device 1. In accordance with a first group of embodiments and a third group of embodiments of the present disclosure, the apparatus 2 is a supplemental device configured to releasably attach to the injection device 1. The present disclosure is not, however, limited to such an arrangement. In accordance with a second group of embodiments of the present disclosure, the apparatus 2 is an integral part of the injection device 1. The above embodiments are described in detail below.

As set out above, according to a first group of embodiments, the injection device 1 comprises an apparatus 2 configured to record information concerning the use of the injection device 1 in the form of a separate supplementary device 2 configured to releasably attach to the injection device 1.

FIG. 2 shows an exemplary supplementary device 2 to be releasably attached to the injection device 1 of FIG. 1. The skilled person would understand that a variety of supplementary devices could be employed. For instance, WO2016/131713A1, WO2016/142511A1, and WO2016/198616A1 all describe supplementary devices comprising a mating unit for releasably attaching the device to an injection device. As shown in FIGS. 2A and 2B, the supplementary device 2 may also be attached to the injection device 1 at a variety of locations or in different positions, in order to record information concerning the use of the injection device 1.

The supplementary device 2 comprises a housing 20 with a mating unit configured to embrace the housing 10 of the injection device 1 of FIG. 1, so that the supplementary device 2 sits tightly on housing 10 of the injection device 1, but is nevertheless removable from the injection device 1. In some examples, the dosage window 13 of the injection device 1 is obstructed by the supplementary device 2 when attached to the injection device 1.

The supplementary device 2 of FIG. 2 also includes a label 30 provided in association with the supplementary device 2. The label 30 is presently exemplified in FIG. 2 as being provided on the housing 20 of the supplementary device 2, but the present disclosure is not limited to this arrangement. It will be appreciated that a variety of labels may be provided. The label 30 may be integrally formed, for instance printed, on the outer surface of the housing 20 of the supplementary device 2. Alternatively, the label 30 may be removably attached to the supplementary device 2, for instance, in the form of a sticker. Alternatively, the label 30 may equally well be provided in combination with the packaging of one or more supplementary devices. The packaging may include a number of labels each for respective ones of the supplementary devices in the pack or a single label applicable to all of the supplementary devices in the pack.

The label 30 provides information relating to the supplementary device 2. In particular, the label 30 includes a first security code 602 that is unique to the supplementary device 2. The first security code 602 may take any suitable form, for instance, the first security code 602 is a key seed code. The label 30 is provided as part of a two-factor authentication system to enable the supplementary device 2 to broadcast information securely and for this information to be received by another device. The first security code 602 is one factor of the two-factor authentication system for allowing generation of a cryptographic key 605, as will be described in more detail below.

In some examples, the supplementary device 2 may comprise a display 21. Information is displayed via the display 21 of the supplementary device 2 for use by the user of the injection device 1. The display 21 may be of any suitable type, such as a Liquid Crystal Display (LCD) or a touch-screen display to receive user input, for instance.

Figure 3:
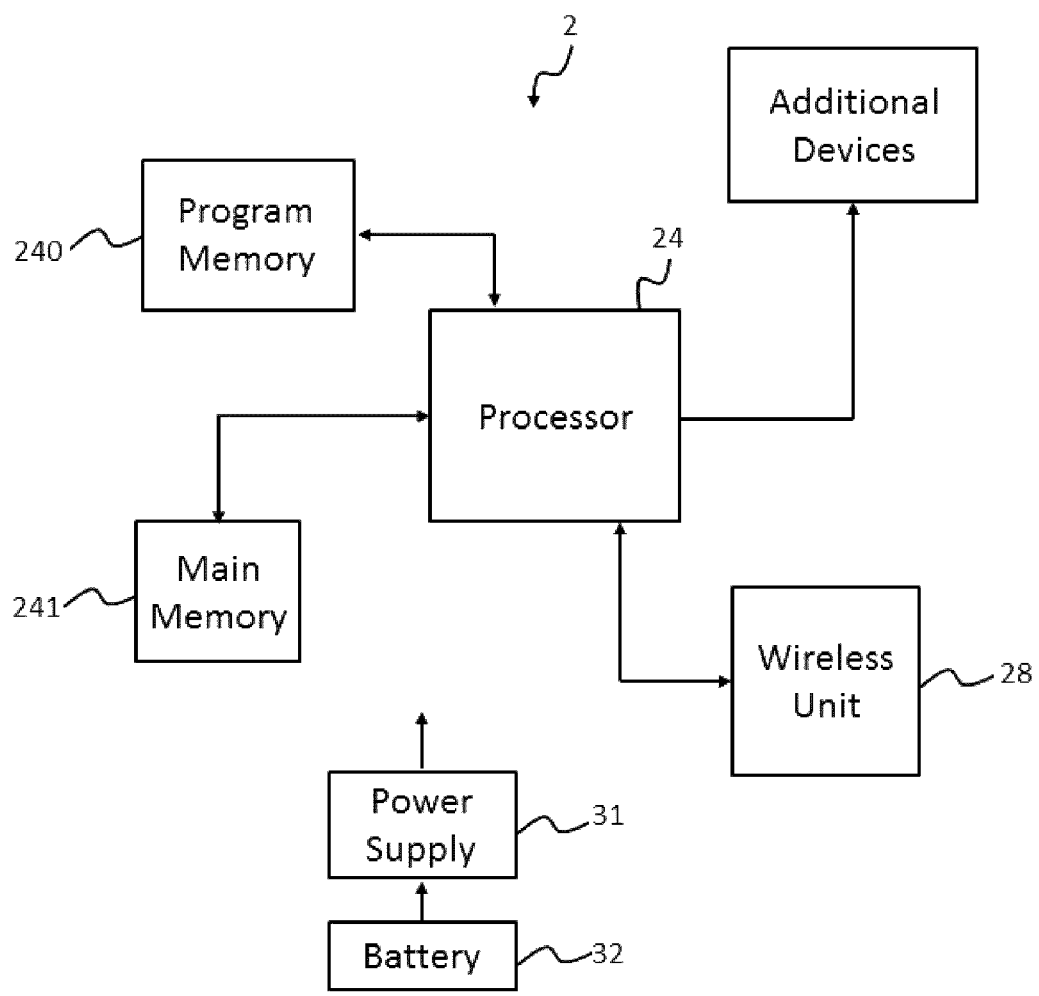
FIG. 3 is a schematic view of a sensor device, as shown in FIG. 2, showing internal components of the sensor device.

Some of the internal components of the supplementary device 2 are shown in FIG. 3. These are contained within the housing 20 of the supplementary device 2. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240. Program memory 240 may for instance be a Read-Only Memory (ROM) or Flash memory.

The processor 24 also uses a main memory 241 and the main memory 241 may for instance be a Random Access Memory (RAM). The main memory 241 may store, for instance, intermediate results. The main memory 241 also stores the second security code 604 specific to the supplementary device 2. The second security code 604 represents the second security code 604 required to generate the cryptographic key 605. The second security code 604 may, for instance, be provided on manufacture of the supplementary device 2. The second security code 604 may be a salt code. The first security code 602 is the security code provided by the label 30. The second security code 604 is one factor of a two-factor authentication system for allowing generation of a cryptographic key 605, as will be described in more detail below.

The main memory 241 may further store a cryptographic key 605 (or crypto key) that is specific to the supplementary device 2. The cryptographic key 605 may, for instance, be provided on manufacture of the supplementary device 2. The cryptographic key 605 represents a symmetric encryption key. The cryptographic key 605 may be in accordance with Advanced Encryption Standard (AES) 128. The cryptographic key 605 is generated by the first security code 602 and the second security code 604 using a standard hash function and is described in more detail below.

The processor 24 controls the plurality of components contained in the supplementary device 2. The supplementary device 2 may include a variety of components configured to record information concerning the use of the injection devices, for instance a display, an optical sensor or one or more internal (contact or non-contact based) movement sensors, but such components will not be described in detail here. The supplementary device 2 of FIG. 3 is thus, capable of capturing information related to a condition and/or use of the injection device 1.

The processor 24 further controls a wireless communication unit 28, which is configured to transmit and/or receive information to/from another device in a wireless fashion. The wireless communication unit 28 is presently embodied as a Bluetooth Low Energy (BLE) transceiver, although other communication protocols may be used. At least some of the information captured by the supplementary device 2 may be transmitted wirelessly to another device. Furthermore, processor 24 may enable at least some of the transmitted information to be encrypted using the cryptographic key 605 stored in the main memory 241.

The supplementary device 2 shown in FIG. 2 is merely described as an example of a supplementary device. Alternative supplementary devices configured to releasably attach to the injection device 1 may equally well be implemented, as set out above.

According to a second group of embodiments, there is provided an injection device 1 that is substantially the same as that shown in FIG. 1.

In accordance with the second group of embodiments, however, the injection device 1 of FIG. 1 also includes a label 30 (not shown) provided in association with the injection device 1. The label 30 is presently exemplified as being provided on the housing 10 of the injection device 1 (see FIG. 4B), but the present disclosure is not limited to this arrangement. It will be appreciated that a variety of labels may be provided. The label 30 may be integrally formed, for instance printed, on the outer surface of the housing 10 of the injection device 1. Alternatively, the label may be removably attached to the injection device 1, for instance, in the form of a sticker. Alternatively, the label 30 may equally well be provided in combination with the packaging of one or more the injection devices. The packaging may include a number of labels each for respective ones of the injection devices in the pack or a single label applicable to all of the injection devices in the pack.

The label 30 provides information relating to injection pen 1 and/or the medicament provided therein. In particular, the label 30 includes a first security code 602 that is unique to injection pen 1. The first security code 602 may take any suitable form, for instance, the first security code 602 is a key seed code. The first security code 602 is provided as part of a two-factor authentication system to enable secure synchronisation between the injection device 1 and another device and will be described in more detail below.

According to the second group of embodiments, the injection device 1 also comprises an apparatus 2 configured to record information concerning the use of the injection device 1 that is integrally formed with the injection device 1.

The apparatus 2 when integrally formed with the injection device 1 comprises substantially the same components and capabilities as the supplementary device 2 described above in relation to the first group of embodiments (see FIG. 3) and will not therefore be repeated in detail here. In brief, however, the apparatus 2 includes, for instance, at least one or more sensors for providing information indicative of how the injection device 1 is used, a processor 24 configured to analyse that use information, a transmitter 28 for wirelessly transmitting the use information to a remote device and a main memory 241 for storing the use information, a cryptographic key 605 and a second security code 604. In contrast, however, as the apparatus 2 is integrally formed with the injection device 1, the housing 10 of the injection device 1 forms the housing of the apparatus 2. As such, the label 30 is described as being provided in association with the injection device 1, rather than apparatus 2 directly (see FIG. 4B).

Figure 4A:
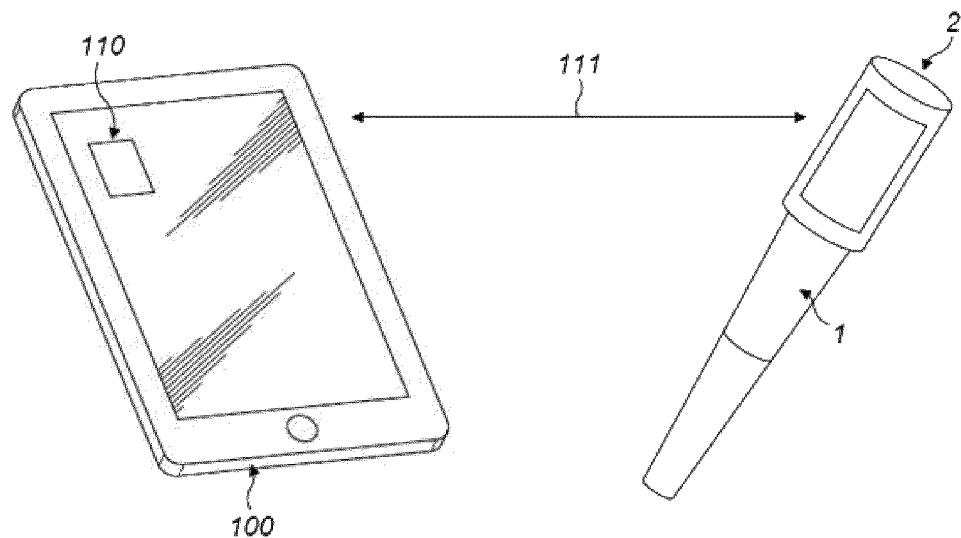
In FIG. 4A the apparatus is a supplementary device attached to the drug delivery device of FIG. 1.
Figure 4B:
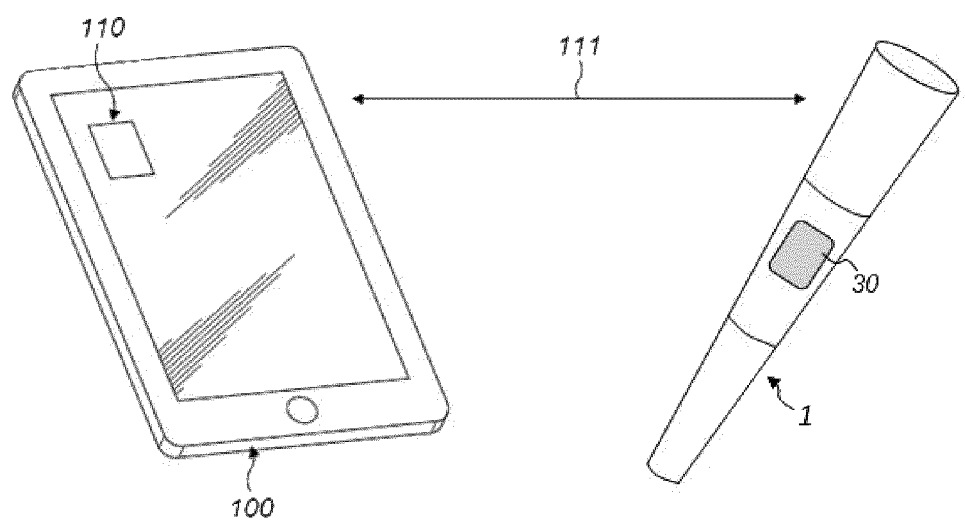
In FIG. 4B the apparatus is integrally formed with the drug delivery device of FIG. 1.

FIG. 4 shows a mobile device 100, such as a smartphone, being used in conjunction with the apparatus 2. Specifically, FIG. 4A shows the mobile device 100 being used in conjunction with the supplementary device 2 of the first group of embodiments when attached to the injection device 1. FIG. 4B shows the mobile device 100 being used in conjunction with the apparatus 2 of the second group of embodiments, in which apparatus 2 (not shown) is integrally formed with the injection device 1. The mobile device 100 is programmed in a suitable way, for instance by being provided with a suitable software application 110. The mobile device 100 in FIGS. 4A and 4B is substantially the same.

In brief, the system of the mobile device 100 and the apparatus 2, functions to record a medicament dosage when the injection device 1 is used. The apparatus 2 communicates with the mobile device 100 using a predefined communication interface 111. The user interacts primarily with supplementary device 2 according to the first group of embodiments and the injection device 1 according to the second group of embodiments. The mobile device 100 serves primarily to record the user's injection history, in other words a series of dose records that form their medication dose history. The apparatus 2 transmits data in the form of an encrypted payload (or data packet) to the mobile device 100, via the predefined communication channel 111 (FIG. 4). The mobile device 100 receives, decrypts and records the medicament administration information (e.g. dose record). A more detailed explanation of how the system is configured and functions is described below.

Figure 5:
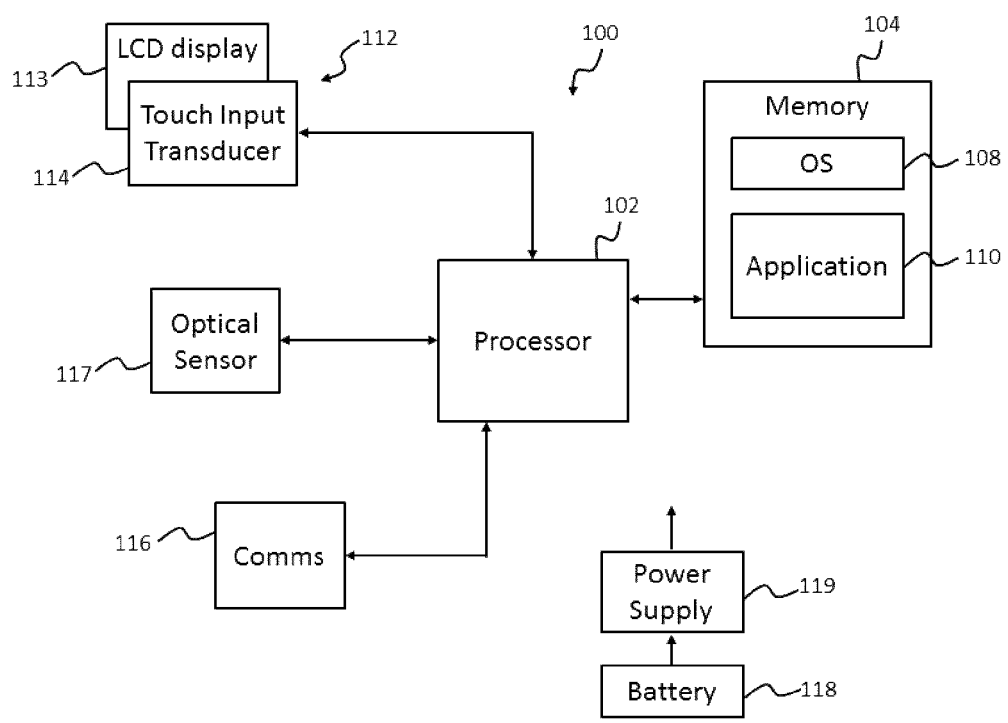
FIG. 5 is a schematic view of the mobile device of FIG. 4, showing internal components of the mobile device according to embodiments of the present disclosure.

Some of the internal components of the mobile device 100 are shown in FIG. 5. The mobile device 100 includes a processor 102. The processor 102 controls operation of the other hardware components of the mobile device 100. The processor 102 and other hardware components may be connected via a system bus (not shown). Each hardware component may be connected to the system bus either directly or via an interface.

The mobile device 100 comprises a memory 104, i.e. a working or volatile memory, such as RAM, and a non-volatile memory. The non-volatile memory stores an Operating System (OS) 108 and a medicament administration monitoring function 110 that is able to store data files and associated metadata. Advantageously, the medicament administration monitoring function 110 is a discrete application or software module that is distinct from other software modules of the mobile device 100. As a discrete component, the medicament administration monitoring application 110 may be provided as a software application in the mobile device 100 on manufacture or it may be downloaded into the mobile device 100 by a user, for instance from an application market place or application store. The software application may be a smartphone app comprising a computer program to perform a medicament administration monitoring function, as described below.

The mobile device 100 comprises a display 112 (for instance an LCD, TFT (thin film transistor), OLED (organic light emitting diode), ePaper). The display may be a touch sensitive display having a display part 113 and a tactile interface part 114. The mobile device 100 also includes a communications interface 116, such as a BLE interface, which is configured to transmit and/or receive information to/from another device in a wireless fashion. The mobile device 100 may include an optical sensor 117, e.g. a camera, for instance for capturing images and scanning optical labels. The mobile device 100 also houses a battery 118 to power the mobile device 100 by a power supply 119.

The processor 102 is configured to send and receive signals to and from the other components in order to control operation of the other components. For example, the processor 102 controls the display of content on the display 112 and receives signals as a result of user inputs, for instance from the tactile interface 114. The display 112 may be a resistive touch screen or capacitive touch screen of any kind. Alternatively, the display 112 may not be a touch screen, for instance, it may equally be an LCD.

The mobile device 100 may be a mobile phone such as a smartphone, PDA or tablet computer of any kind. Other standard or optional components of the mobile device 100, such as transceivers, are omitted from description. The processor 102 may be an integrated circuit of any kind. The processor 102 may access RAM in order to process data and may control the storage of data in memory 104. Memory 104 may be a non-volatile memory of any kind, such as a ROM, a flash memory and a magnetic drive memory. The RAM may be a RAM of any type, for example Static RAM (SRAM), Dynamic RAM (DRAM) or a Flash memory.

The processor 102 operates under control of the OS 108. The OS 108 may comprise code relating to hardware, such as the display 112 and the communications interface 116, as well as the basic operation of the mobile device 100. The OS 108 may also cause activation of other software modules stored in the memory 104, such as the medicament administration monitoring function 110. The medicament administration monitoring software application 110 comprises program code according to aspects of the present disclosure.

Figure 6:
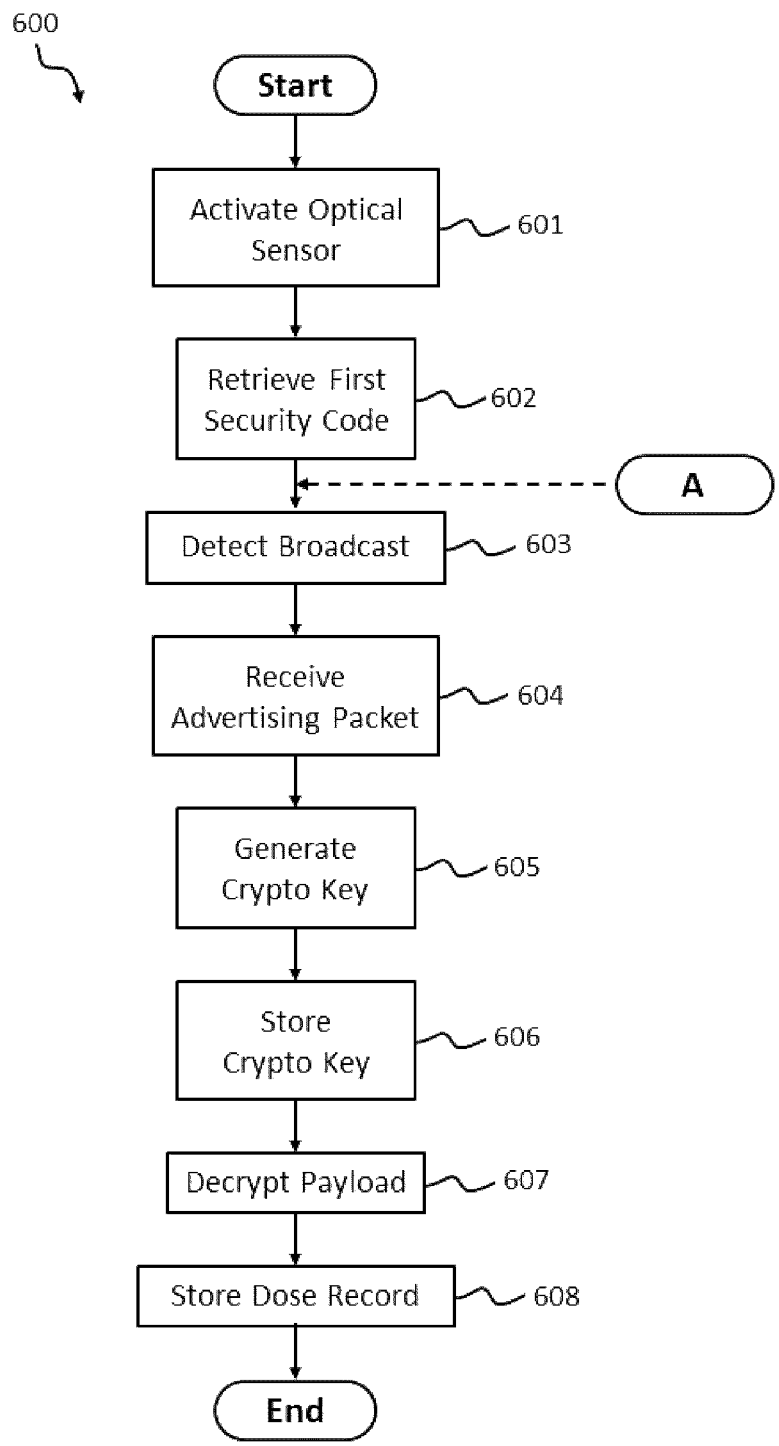
FIG. 6 is a flow chart showing operation of the mobile device of FIG. 4 when used in conjunction with the apparatus according to embodiments of the present disclosure.
Figure 7:
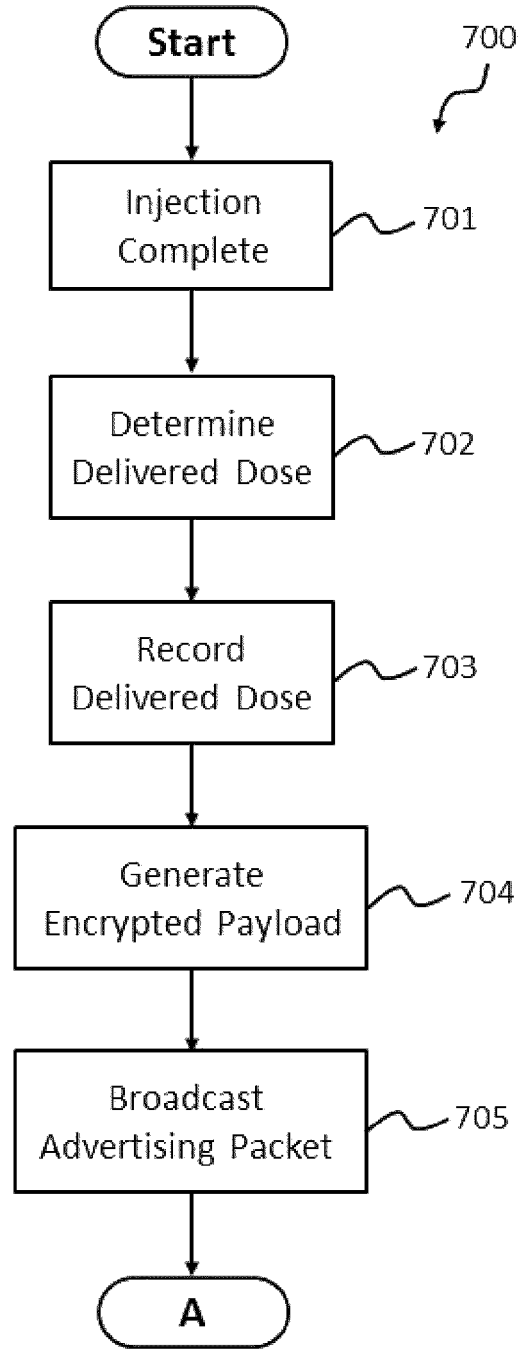
FIG. 7 is a flow chart showing operation of the apparatus when used in conjunction with the mobile device of FIG. 4 according to embodiments of the present disclosure.
Figure 8:
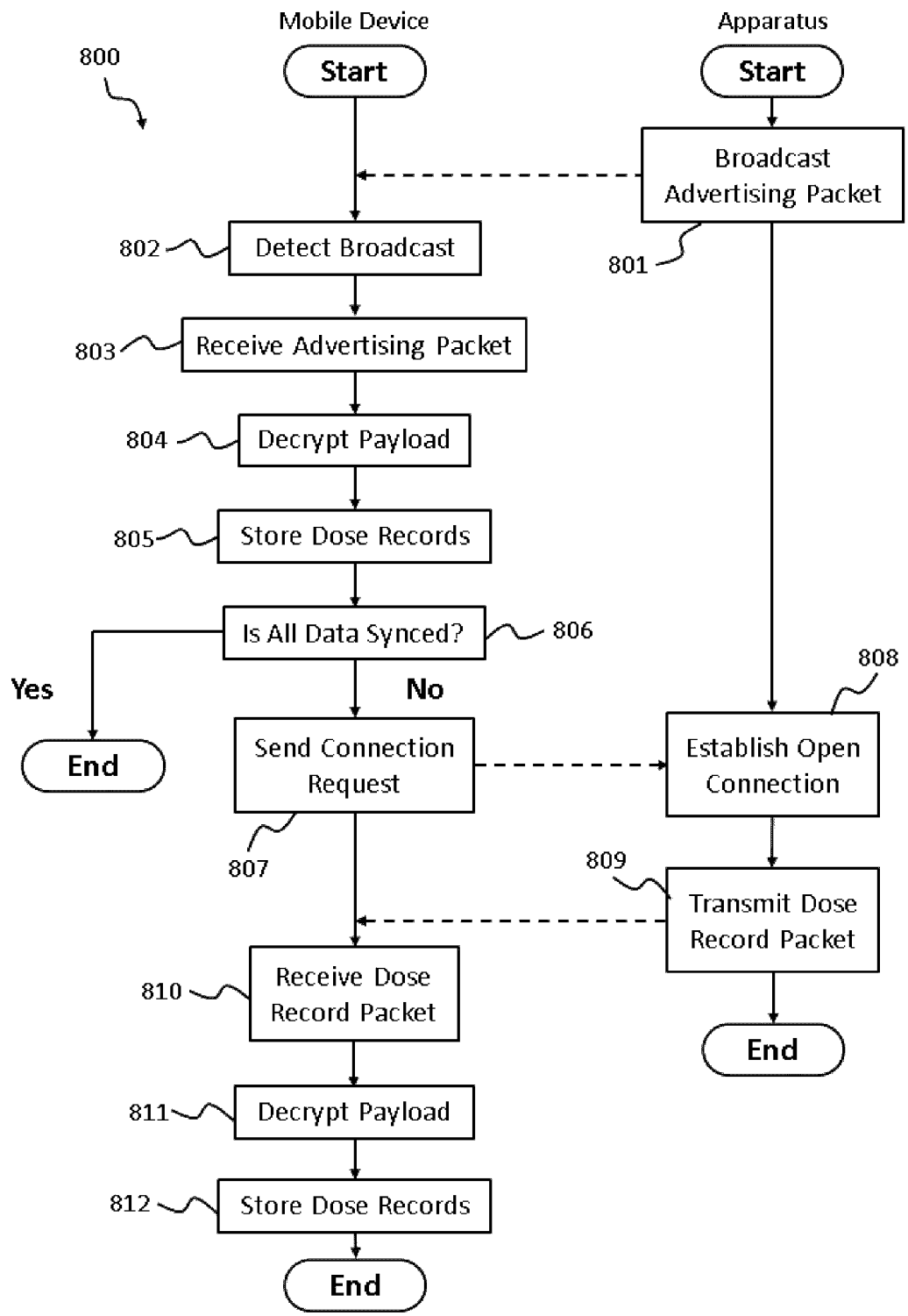
FIG. 8 is a flow chart showing operation of the mobile device of FIG. 4 and the apparatus according to embodiments of the present disclosure.

FIGS. 6 to 8 are flow charts illustrating the monitoring system according embodiments of the present disclosure. The flow charts illustrate how the apparatus 2 and the mobile device 100 interact and operate as a system in accordance with embodiments of the present disclosure.

In relation to the mobile device 100, the steps of FIGS. 6 to 8 are performed by the optical sensor 117 and the communications interface 116 under control of the processor 102 under control of the software application 110 stored in the memory 104. The software application 110 is presently embodied as the medicament administration monitoring function. In relation to the apparatus 2, the steps of FIGS. 6 to 8 are performed by the processor 24 of apparatus 2 under control of the software stored in the memory 240.

In the context of the first group of embodiments, FIGS. 6 and 7 are flow charts illustrating respectively, the operation of the mobile device 100 and the supplementary device 2 during an initial syncing operation. The initial syncing operation may occur when a new supplementary device 2 is selected for the first time for use with the injection device 1 or where it is necessary to manually re-sync the mobile device 100 with the supplementary device 2. The intention of the initial sync operation is for the mobile device 100 to generate the cryptographic key 605 (crypto key) of the supplementary device 2, such that the supplementary device 2 and the mobile device 100 become known to each other.

In FIG. 6, the operation 600 starts, for instance, when the supplementary device 2 is turned on or is otherwise activated when it is selected for initial use (or to perform a re-syncing operation) with the mobile device 100. In step 601, the processor 102 of the mobile device 100 controls the optical sensor 117 to scan the label 30 of the supplementary device 2. The label 30 is presently embodied as a Quick Response (QR) code provided on the housing 20 of the supplementary device 2 (FIG. 2). The QR code includes a first security code 602, for instance a key seed code, which is unique to the supplementary device 2. The first security code 602 is not stored in the main memory 241 of the supplementary device 2. The first security code 602 may be of any suitable type, for instance an alphanumeric code having multiple characters, for instance six to ten characters. The QR code may additionally include an identification number, for instance a Device ID, for the supplementary device 2, although this is not essential. The identification number may uniquely identify the supplementary device 2. A hash function may be applied, for instance at least once, to the identification number. The hash function may be of any suitable type.

The first security code 602 is presently embodied as a key seed code in the form of a QR code, but the present disclosure is not limited to such a form. The key seed code 602 may equally well be provided by another machine readable optical label, for instance a barcode. Alternatively, the key seed code 602 may be printed, for instance as a numeric or alphanumeric. Similarly, the present disclosure is not limited to the use of the optical sensor 117. Near-field communication (NFC) technology, for instance, could equally well be used to identify and transmit the key seed code 602. Alternatively, step 601 may be omitted and the user may manually enter the first security code 602 of the supplementary device 2.

The provision of a label 30 having the key seed code 602 on the housing 20 of the supplementary device 2 allows any device that has scanned the label 30 to decrypt payloads or data packets of the supplementary device 2. This can be advantageous should it be necessary to employ multiple devices or multiple different devices, such as a tablet and a smart phone, to keep a record of the user's medication dose history. Thus using multiple devices and/or switching to new device is easy and possible. Additionally, the fact that the label 30 may be removed and disposed of minimises the opportunity for malicious devices to scan the label 30 and determine the key seed code 602 of the supplementary device 2, which in turn could enable the malicious device to intercept encrypted payloads.

In step 602, the key seed code 602 is retrieved from the label 30 and received at the mobile device 100. The retrieval or transmission of the key seed code 602 occurs out of band. In other words, the transmission of the key seed code 602 does not occur using BLE communication, for instance, an open BLE connection is not established. Instead, the retrieval of the first security code 602 requires the supplementary device 2 and the mobile device 100 to be physically proximal to each other to enable the two devices to sync with each other. This is advantageous as it reduces the likelihood of other malicious devices pairing with the supplementary device 2 or intercepting transmitted payloads, thereby increasing the security of the user's medication dose history.

Once the key seed code 602 has been retrieved, the user may proceed to use the injection device 1 for the first time to administer a dose of medicament. FIG. 7 shows the steps that occur at the supplementary device 2 after the user has used the injection device 1 for the first time to administer a dose of medicament. FIG. 7 is shown separately for reasons of clarity only.

In FIG. 7, the operation 700 starts at step 701, when the processor 24 detects that an input, indicating that the injection process is complete, has been provided at the supplementary device 2. In step 702, the processor 24 controls those components of the supplementary device 2 configured to record information concerning the use of the injection device 1 and accordingly, determines the dose dialled, which is regarded to be the delivered dose. In step 703, the delivered dose is recorded in the main memory 241 of the supplementary device 2. The recorded information represents a dose record.

Although it is described that the user uses the injection device 1 for the first time to administer a dose of medicament after the mobile device 100 has retrieved the key seed code 602, the disclosure is not limited to this. The user may equally administer a dose of medicament for the first time and then subsequently perform step 601 and/or step 602 at the mobile device 100 to retrieve the key seed code 602.

Once the dose record has been recorded, in step 704, the processor 24 of the supplementary device 2 encrypts the dose record using the cryptographic key 605 of the supplementary device 2, thereby generating an encrypted payload. The cryptographic key 605 may be stored in the main memory 241 of the supplementary device 2. The encrypted payload includes the dose record detailing the dose of medicament injected by the user on first use of the supplementary device 2 with the injection device 1. The encrypted payload and/or the dose record may also include further information relating to the operation of the injection device 1, for instance, information relating to the date and/or time of the ejected dose and/or a dose sequence number.

In step 705, after the completion of the injection process, the processor 24 of the supplementary device 2 controls the wireless communication unit 28 to broadcast a packet 705, for instance an advertising packet. The advertising packet 705 is broadcast via Bluetooth, for instance via BLE. The advertising packet 705 includes the encrypted payload having the dose record as described above, in addition to a second security code 604, for instance a salt code. The second security code 604 is unique to the supplementary device 2. The advertising packet 705 may further include an identification number for the supplementary device 2, as described above, but this is not essential.

Returning to FIG. 6, in step 603, the mobile device 100 is able to detect the broadcast of the supplementary device 2. This is because, for instance, the mobile device 100 is in proximity to the supplementary device 2. The mobile device 100 thereby receives the advertising packet 705, including the encrypted payload and the salt code 604 from the supplementary device 2 in step 604. When the mobile device 100 has received the second security code 604, the software application 110 has the required information to determine the cryptographic key 605 that is unique to the supplementary device 2.

Although it is described that the advertising packet 705 includes the second security code 604, the disclosure is not limited to this. Alternatively, the second security code 604 may be broadcast separately to the advertising packet 705 having the dose record. Alternatively, not every advertising packet 705 is required to include the second security code 604. For instance, the first advertising packet 705 broadcast during the initial sync operation includes the second security code 604 but it is not necessary for each subsequent advertising packet 705 to include the second security code 604. However, the mobile device 100 is able to receive the second security code 604 without requiring an open connection with the supplementary device 2. An open connection is only required for the missing dose record packet 810 or a key exchange, which is described in detail below.

Although it is described that the second security code, or salt code, 604 is included in the advertising packet 705, the disclosure is not limited to this. Alternatively, only the encrypted payload is included in the advertising packet 705 broadcast by the supplementary device 2 and the second security code 604 may be broadcast by the supplementary device 2 separately to the advertising packet 705 on demand from the mobile device 100.

In step 605, the software application 110 generates the cryptographic key 605 of the supplementary device 2 using the first security code 602 and the second security code 604 of the supplementary device 2 and a standard hash function. That is, the software application 110 generates the cryptographic key 605 of the supplementary device 2 using the key seed code 602 and the salt code 604 of the supplementary device 2 and a standard hash function. The hash function may be applied once or it may be applied multiple times, as required. The hash function may be of any suitable type. The cryptographic key 605 may be in accordance with AES 128.

It is described that the first security code 602 is a key seed code and the second security code 604 is a salt code, but the present disclosure is not limited to this arrangement. The first security code 602 may equally be a salt code and the second security code 604 may be a key seed code.

In step 606, the cryptographic key 605 is stored in the memory 104 of the mobile device 100. The mobile device 100, via the software application 110, is then able to decrypt any encrypted payload transmitted between the supplementary device 2 and the mobile device 100, based on the cryptographic key 605 of the supplementary device 2. Similarly, the mobile device 100 is also able to encrypt data or commands transmitted to the supplementary device 2 using the cryptographic key 605 of the supplementary device 2.

Advantageously, no native BLE or Bluetooth security features are used. Instead, the present disclosure provides a more secure, two-factor authentication system, requiring the use of a key seed code 602 that is not stored in the main memory 241 of the supplementary device 2, in combination with a salt code 604 that is stored in the main memory 241 of the supplementary device 2. Thus, security is handled on the software application 110 (data layer) so that the BLE communication is simple and compliant with BT SIG standards. This improves the security of the user's medication dose history as it at least requires any attacker to gain physical access to the supplementary device 2 and record advertising traffic. The present disclosure also ensures that dose records are always encrypted and cannot be easily intercepted by malicious software applications on the mobile device 100.

Accordingly, in step 607, the software application 110 of the mobile device 100 decrypts the encrypted payload using the generated cryptographic key 605 and thereby accesses the dose record. In step 608, the dose record is stored as part of a medication dose history in the memory 104 of the mobile device 100.

The fact that decryption is done within the software application 110 is advantageous as malicious applications can only intercept encrypted data and do not have access to the decrypted data (i.e. the dose records). The dose records are therefore more secure and cannot be easily stolen or modified.

In the present disclosure, the provision of the cryptographic key 605 enables symmetric encryption at both the supplementary device 2 and the mobile device 100 of any payload to be transmitted between the supplementary device 2 and the mobile device 100. Advantageously, this enables the transfer of dose records to occur more securely as the process of data transmission is independent of the exact contents of the payload itself. In addition, patient identification data is never transmitted to or stored at the supplementary device 2.

The system also allows for minimal interaction from a user, as once the mobile device 100 has stored the unique cryptographic key 605, the mobile device 100 is able to receive subsequent payloads automatically and more securely, without the need to pair to the supplementary device 2 over an open network.

FIG. 8 is a flowchart of the operation of the mobile device 100 and the apparatus 2 when determining whether there is a need to update the dose records of the user's medication dose history stored in the memory 104 of the mobile device 100. The steps of the flowchart may be carried out automatically by the mobile device 100 or manually by a user operating the mobile device 100. This occurs when the mobile device 100 and the apparatus 2 are already known to each other, that is, they have already been synced in accordance with FIGS. 6 and 7, for instance.

In the context of the first group of embodiments, FIG. 8 illustrates the operation of the mobile device 100 and the supplementary device 2. In FIG. 8, operation 800 starts at step 801 when the wireless communication unit 28 of the supplementary device 2 is activated to broadcast an advertising packet 705. The advertising packet 705 is broadcast via Bluetooth, for instance via BLE.

The supplementary device 2 may broadcast the advertising packet 705 after a dose of medicament has been administered. The supplementary device 2 may, for instance, broadcast the advertising packet 705 after the completion of each injection process. In this instance, the dose record is always the latest dose record. Alternatively, however, the supplementary device 2 may only broadcast an advertising packet 705 in response to a Connection Request received from the mobile device 100.

In addition, after a predetermined period of time, the supplementary device 2 may cease to broadcast the advertising packet 705 and/or may return to a standby state or turn off (not shown). This is advantageous as it enables the supplementary device 2 to save power when the mobile device 100 is not available to receive the advertising packet 705.

The advertising packet 705 includes at least an encrypted payload having a dose record. The generation of the advertising packet 705 may be substantially similar to the steps shown in FIG. 7. In accordance with FIG. 7 (step 704), the advertising packet 705 may include an encrypted payload and the second security key. Alternatively, the advertising packet 705 does not include the second security key. In this instance, the supplementary device 2 only sends the second security key 604 in response to a request from the mobile device 100.

In step 802, the mobile device 100 detects that the supplementary device 2 is broadcasting an advertising packet 705. The mobile device 100 thereby receives the advertising packet 705, including the encrypted payload from the supplementary device 2 in step 803.

In step 804, the software application 110 of the mobile device 100 decrypts the encrypted payload using the stored cryptographic key 605 of the supplementary device 2 and thereby accesses the dose record. As detailed above, the cryptographic key 605 is generated and stored in the memory 104 of the mobile device 100 during initial synchronisation with the supplementary device 2 (see FIGS. 6 and 7). In step 805, the dose record is stored as part of a medication dose history in the memory 104 of the mobile device 100.

When the mobile device 100 has decrypted and stored the received dose record in step 805, the software application 110 determines whether the dose records stored in the memory 104 of the mobile device 100 are complete in step 806. That is, the software application 110 determines whether a previous dose record is missing from the sequence of stored dose records.

For instance, in an example where the mobile device 100 has been out of range of the supplementary device 2 during a period of time in which more than one instance of medicament dose delivery (i.e. injection) has occurred, then the mobile device 100 may be missing one or more previous dose records. When the software application 110 of the mobile device 100 has decrypted and stored the latest dose record in step 805, the software application 100 may determine in step 806 that the latest stored dose record is, for instance, the fifth dose record, that is it is the fifth sequential dose record generated by the supplementary device 2.

Accordingly, the software application 110 may determine that the previous stored dose record is, for instance, the first dose record in the sequence. The software application 110 thereby determines that a dose record is missing. In this example more than one consecutive dose record is missing, namely the second, third and fourth dose records are missing. The software application 110 therefore is configured to try and obtain the missing dose records, in order to ensure that the record of the medication dose history is complete.

In step 806, if it is determined that 'No' the medication dose history is not complete, such that the mobile device 100 requires more dose records as one or more previous dose records is missing, then, in order to sync all the dose records, the mobile device 100 sends a Connection Request to the supplementary device 2 in step 807. To send a Connection Request, the communications interface 116 of the mobile device 100 is activated, that is a BLE communication channel 111 is established.

The Connection Request includes at least an encrypted command requesting connection to the supplementary device 2 and receipt of the missing dose records in the form of a packet 810, for instance a dose record packet (update packet), from the supplementary device 2. The Connection Request is encrypted using the cryptographic key 605 specific to the supplementary device 2. The Connection Request is sent via an open communication channel 111, for instance via an open BLE connection.

In step 808, the processor 24 of the supplementary device 2 detects the open communication channel 111 of the mobile device 100 and receives the Connection Request and request for the dose record packet 810. In step 809, the supplementary device 2 transmits the dose record packet 810 to the mobile device 100 via the open communication channel 111, for instance via the open BLE connection.

In step 810, the mobile device 100 receives the dose record packet 810 from the supplementary device 2. The dose record packet 810 includes an encrypted payload having the one or more missing dose records, as required. That is, the encrypted payload includes any dose records not previously sent to the mobile device 100. In step 811, the software application 110 decrypts the encrypted payload using the cryptographic key 605 of the supplementary device 2, the cryptographic key 605 having been generated and stored during initial synchronisation with the supplementary device 2 (see FIGS. 6 and 7). In step 812, the missing dose record(s) are stored in the memory 104 of the mobile device 100.

In accordance with FIG. 8, the supplementary device 2 may broadcast an advertising packet 705 after the completion of each injection process. Alternatively, however, the supplementary device 2 may only broadcast an advertising packet 705 in response to a Connection Request received from the mobile device 100.

In FIG. 8, if it is determined in step 806 that 'Yes' the medication dose history is complete, that is a continuous sequence of dose records is stored in the medication dose history, such that all the dose records are synced, then the mobile device 100 does not require any dose records and the operation ends.

This system is advantageous as it reduces unwanted traceability of encrypted payloads, it saves energy consumption of the supplementary device 2 and it allows multiple use events of the injection device 1.

Although the methods of FIGS. 6, 7 and 8 has been described above in the context of the supplementary device 2 and the mobile device 100 according to the first group of embodiments, the present disclosure is not limited to such an arrangement. FIGS. 6 to 8 may equally apply to the operation of the apparatus 2 and the mobile device 100 according to the second group of embodiments, as set out below. In the second group of embodiments, the apparatus 2 is integrally formed with the injection device 1, as described above. As such, in the context of the second group of embodiments, reference to the operation of the injection device 1 is a reference to the operation of the apparatus 2 as integrally formed in the injection device 1. The same alternatives and advantages described in relation to the components of the first group of embodiments will also be apparent in the second group of embodiments and will not therefore be described again below.

In the context of the second group of embodiments, FIGS. 6 and 7 are flow charts illustrating the operation of the mobile device 100 and the apparatus 2 of the injection device 1 during an initial syncing operation. The initial syncing operation may occur when a new injection device 1 is selected for use for the first time or where it is necessary to manually re-sync the mobile device 100 with the injection device 1. The intention of the initial sync operation is for the mobile device 100 to generate the cryptographic key 605 of the injection device 1, such that the injection device 1 and the mobile device 100 become known to each other.

In FIG. 6, the operation 600 starts, for instance, when the injection device 1 is first selected for initial use (or to perform a re-syncing operation) with the mobile device 100. In step 601, the processor 102 of the mobile device 100 controls the optical sensor 117 to scan the label 30 of the injection device 1. The label 30 is embodied as a Quick Response (QR) code provided on the housing 10 of the injection device 1. The QR code includes a first security code 602, for instance a key seed code, which is unique to the injection device 1 and is not stored in the memory 241 of the injection device 1. The first security code 602 may be of any suitable type, for instance an alphanumeric code having multiple characters, for instance six to ten characters. The QR code may additionally include an identification number, for instance a Pen ID, for the injection device 1, although this is not essential. The identification number uniquely identifies the injection device 1. A hash function may be applied, for instance at least once, to the identification number. The hash function may be of any suitable type.

In step 602, the key seed code 602 has been retrieved from the label 30 and received at the mobile device 100. The retrieval or transmission of the key seed code 602 occurs out of band. In other words, the transmission of the key seed code 602 does not occur using BLE communication, for instance, an open BLE connection is not established. Instead, the retrieval of the first security code 602 requires the injection device 1 and the mobile device 100 to be physically proximal to each other to enable the two devices to sync with each other.

Once the key seed code 602 has been retrieved, the user may proceed to use the injection device 1 for the first time to administer a dose of medicament. FIG. 7 shows the steps that occur at the injection device 1 after the user has used the injection device 1 for the first time to administer a dose of medicament. FIG. 7 is shown separately for reasons of clarity only.

In FIG. 7, the operation 700 starts at step 701, when the injection device 1 is turned on or is otherwise activated and the processor 24 detects that a user input, indicating that the injection process is complete, has been provided. In step 702, the processor 24 controls those components of the supplementary device 2 configured to record information concerning the use of the injection device 1 and accordingly, determines the dose dialled, which is regarded to be the delivered dose In step 703, the delivered dose is recorded in the main memory 241 of the supplementary device 2. The recorded information represents a dose record.

Once the dose record has been recorded, in step 704, the processor 24 encrypts the dose record using the cryptographic key 605 of the injection device 1, thereby generating an encrypted payload. The cryptographic key 605 may be stored in the main memory 241 of the injection device 1. The encrypted payload includes the dose record detailing the dose of medicament injected by the user on first use of the injection device 1. The encrypted payload and/or the dose record may also include further information relating to the operation of the injection device 1, for instance, information relating to the date and/or time of the ejected dose and/or a dose sequence number.

In step 705, after the completion of the injection process, the processor 24 of the injection device 1 controls the wireless communication unit 28 to broadcast a packet, for instance an advertising packet 705. The advertising packet 705 is broadcast via Bluetooth, for instance via BLE. The advertising packet 705 includes the encrypted payload having the dose record as described above, in addition to a second security code 604, for instance a salt code. The second security code 604 is unique to the injection device 1. The advertising packet 705 may further include an identification number for the injection device 1, as described above, but this is not essential.

Returning to FIG. 6, in step 603, the mobile device 100 is able to detect the broadcast of the injection device 1. This is because, for instance, the mobile device 100 is in proximity to the injection device 1. The mobile device 100 thereby receives the advertising packet 705, including the encrypted payload and the salt code 604 from the injection device 1 in step 604. When the mobile device 100 has received the second security code 604, the software application 110 has the required information to determine the cryptographic key 605 that is unique to the injection device 1.

In step 605, the software application 110 generates the cryptographic key 605 of the supplementary device 2 using the first security code 602 and the second security code 604 of the injection device 1 and a standard hash function. That is, the software application 110 generates the cryptographic key 605 of the injection device 1 using the key seed code 602 and the salt code 604 of the injection device 1 and a standard hash function. The hash function may be applied once or it may be applied multiple times, as required. The hash function may be of any suitable type. The cryptographic key 605 may be in accordance with AES 128.

In step 606, the cryptographic key 605 is stored in the memory 104 of the mobile device 100. The mobile device 100, via software application 110, is then able to decrypt any encrypted payload transmitted between the injection device 1 and the mobile device 100, based on the cryptographic key 605 for the injection device 1. Similarly, the mobile device 100 is also able to encrypt data or commands transmitted to the injection device 1 using the cryptographic key 605 of the injection device 1.

Advantageously, no native BLE or Bluetooth security features are used. In addition, as Bluetooth bonding is not used, the apparatus 2 will not appear on a list of Bluetooth devices at the mobile device 100, so that the user does not need to manually delete the apparatus 2 information when it is no longer required. This is particularly advantageous where the apparatus 2 is integrally formed with a disposable injection device, for instance.

Accordingly, in step 607, the software application 110 of the mobile device 100 decrypts the encrypted payload using the generated cryptographic key 605 and thereby accesses the dose record. In step 608, the mobile device 100 stores the dose record in the memory 104 as part of a medication dose history of the user.

In the context of the second group of embodiments, FIG. 8 is a flowchart illustrating the operation of the mobile device 100 and the injection device 1 when determining whether there is a need to update the dose records of the user's medication dose history stored in the memory 104 of the mobile device 100. In FIG. 8, the operation 800 starts at step 801 when the wireless communication unit 28 of the injection device 1 is activated to broadcast an advertising packet 705. In step 802, the injection device 1 broadcasts the advertising packet 705. The advertising packet 705 is broadcast via Bluetooth, for instance via BLE.

The advertising packet 705 includes at least an encrypted payload having a dose record. The generation of the advertising packet 705 may be substantially similar to the steps shown in FIG. 7.

In step 802, the mobile device 100 detects that the injection device 1 is broadcasting an advertising packet 705. The mobile device 100 thereby receives the advertising packet 705, including the encrypted payload from the injection device 1 in step 803.

In step 804, the software application 110 of the mobile device 100 decrypts the encrypted payload using the stored cryptographic key 605 of the injection device 1 and thereby accesses the dose record. As detailed above, the cryptographic key 605 is generated and stored in the memory 104 of the mobile device 100 during initial synchronisation with the injection device 1 (see FIGS. 6 and 7). In step 805, the dose record is stored as part of a medication dose history in the memory 104 of the mobile device 100.

When the mobile device 100 has decrypted and stored the received dose record in step 805, the software application 110 determines whether the dose records stored in the memory 104 of the mobile device 100 are complete in step 806. That is, the software application 110 determines whether a previous dose record is missing from the sequence of stored dose records.

For instance, in an example where the mobile device 100 has been out of range of the injection device 1 during a period of time in which more than one instance of medicament dose delivery (i.e. injection) has occurred, then the mobile device 100 may be missing one or more previous dose records. When the software application 110 of the mobile device 100 has decrypted and stored the latest dose record in step 805, the software application 100 may determine in step 806 that the latest stored dose record is, for instance, the fifth dose record, that is it is the fifth sequential dose record generated by the injection device 1. Accordingly, the software application 110 may determine that the previous stored dose record is, for instance, the first dose record in the sequence. The software application 110 thereby determines that a dose record is missing. In this example more than one consecutive dose record is missing, namely the second, third and fourth dose records are missing. The software application 110 therefore is configured to try and obtain the missing dose records, in order to ensure that the record of the medication dose history is complete.

It is determined that 'No' the medication dose history is not complete, such that the mobile device 100 requires more dose records as one or more previous dose records is missing, then, in order to sync all the dose records, the mobile device 100 sends a Connection Request to the supplementary device 2 in step 807. To send a connection request, the communications interface 116 of the mobile device 100 is activated, that is a BLE communication channel 111 is established.

In step 806, if it is determined that 'No' the medication dose history is not complete, such that the mobile device 100 requires more dose records as more than one consecutive dose record is missing, then, in order to sync all the dose records, the mobile device 100 sends a Connection Request to the injection device 1 in step 807. To send a Connection Request, the communications interface 116 of the mobile device 100 is activated, that is a BLE communication channel 111 is established.

The Connection Request includes at least an encrypted command requesting connection to the injection device 1 and receipt of the missing dose records in the form of a packet 810, for instance a dose record packet (update packet) from the injection device 1. The Connection Request is encrypted using the cryptographic key 605 specific to the injection device 1. The Connection Request is sent via an open communication channel 111, for instance via an open BLE connection.

In step 808, the processor 24 of the injection device 1 detects the open communication channel 111 of the mobile device 100 receives the Connection Request for the dose record packet 810. In step 809, the injection device 1 transmits the dose record packet 810 to the mobile device 100 via the open communication channel 111, for instance, via the open BLE connection.

In step 810, the mobile device receives the dose record packet 810 from the injection device 1. The dose record packet 810 includes an encrypted payload having more than one or more missing dose records, as required. That is the encrypted payload includes any dose records not previously sent to the mobile device 100. In step 811, the software application 110 decrypts the encrypted payload using the cryptographic key 605 of the injection device 1, the cryptographic key 605 having been generated and stored during initial synchronisation with the injection device 1 (see FIGS. 6 and 7). In step 812, the missing dose record(s) are stored in the memory 104 of the mobile device 100.

In accordance with FIG. 8, the injection device 1 may broadcast an advertising packet 705 after the completion of each injection process. Alternatively, however, the injection device 1 may only broadcast an advertising packet 705 in response to a Connection Request received from the mobile device 100.

In FIG. 8, if it is determined in step 806 that 'Yes' the medication dose history is complete, that is a continuous sequence of dose records is stored in the medication dose history, such that all the dose records are synced, then the mobile device 100 does not require any dose records and the operation ends.

Although the methods of FIGS. 6, 7 and 8 have been described above in the context of the first and second groups of embodiments, the present disclosure is not limited to such an arrangement. FIGS. 6 to 8 may equally apply to the operation of the supplementary device 2 and the mobile device 100 according to the third group of embodiments.

In accordance with a third group of embodiments, there is provided a supplementary device 2 and a mobile device 100 that corresponds substantially to the first group of embodiments as described above. In the third group of embodiments, however, the supplementary device 2 differs from that described in the first group of embodiments in that the label 30 having the first security code 602 is provided in association with the injection device 1, such that there is a 1:1 relationship between the supplementary device 2 and the injection device 1. In one example, the injection device 1 may be a reusable injection device 1.

The label 30 of the injection device 1 is substantially the same as that described above in association with the second group of embodiments. The mobile device 100 therefore retrieves the first security code from the label 30 of the injection device 1 in accordance with FIG. 6, step 601 and/or step 602. Otherwise, in the third group of embodiments, the components, operations, alternatives and advantages of the supplementary device 2 and the mobile device 100 correspond substantially to that described above in relation to the first group of embodiments and will not be described in detail again.

Various alternatives and modifications will be apparent to the skilled person. Some such variations and modifications will now be described.

Although it is described that the mobile device 100 determines the first security code 602 of the apparatus 2 selected for initial synchronisation, the mobile device 100 is also able to determine and store the first security code 602 of multiple apparatuses 2 at the same time. This is advantageous, for instance, where multiple apparatuses 2 are packaged together, each having their own unique label 30. The mobile device 100 can be used to determine and store the first security code 602 of each apparatus 2 in the package. Thus, when each apparatus 2 is in turn subsequently selected for use, no further user action is needed, as the mobile device 100 has already stored the required first security code 602 for each apparatus 2. This is particularly useful where the apparatus 2 is integrally formed with a disposable injection device 1, and a plurality of injection devices 1 are packaged and supplied together.

In some embodiments, the cryptographic key 605 is used only for initial communications and thereafter, a new key is generated, the new key being used for subsequent communications between the apparatus 2 and the mobile device 100. It has been described that the cryptographic key 605 is generated by the mobile device 100 during initial synchronisation with the apparatus 2. Additionally, after this initial sync, the software application 110 of the mobile apparatus 100 may send a new cryptographic key to the apparatus 2 encrypted with the initial cryptographic key. This enables the apparatus 2 to decrypt the encrypted payload and to store the new cryptographic key in the memory 241, for use in subsequent encryption of payloads. The new cryptographic key may be sent via an open BLE connection.

This is advantageous as it results in 1-to-1 binding between the apparatus 2 and the mobile device 100 and the application software 110, thereby hindering re-pairing with malicious devices. It also ensures that the first security code 602 provided by the label 30 is only valid on first use. This can hinder easy re-pairing, thereby preventing malicious devices with (temporary) physical access to the label 30 from using the first security code 602 to try and intercept encrypted payloads.

The new cryptographic key could be in any suitable form. The new cryptographic key could be computed, for instance, from a user ID or password provided in association with the software application 110 of the mobile device 100.

The new cryptographic key could also be stored remotely, for instance, in a cloud storage device. This is advantageous as it is possible to associate the password to a patient cloud account.

It has been described that the dose record is stored in the memory 104 of the mobile device 100. This is advantageous as it is possible to retain a complete medication dose history at the mobile device 100, without requiring the Internet or the provision of a cloud service. It is, however, feasible to incorporate such elements if desired.

In some embodiments the medication dose history including the user's dose records is stored remotely in a cloud storage device. A copy of the medication dose history can be stored in the cloud storage device. Alternatively, the medication dose history can be entirely stored in the cloud storage device. This is advantageous as it is possible to associate the medication dose history with a patient cloud account, it is possible to access data remotely from the mobile device 100 and the potential loss of data is minimised, for instance should the user lose or damage the mobile device 100.

In some embodiments, a secured application command, for instance an expiry function, is provided. It has been described that the second security code 604 is stored in the memory 241 of the apparatus 2. However, the second security code 604 may be stored in any volatile memory of the apparatus 2 that is not powered off. For instance, the second security code 604 is stored in the volatile memory 240 linked to the real-time clock (RTC) associated with the apparatus 2. The RTC is not powered off so that it can keep time whilst the remaining components of the apparatus 2 are in a standby state. In the event that the battery 32 of the apparatus 2 is depleted, just prior to depletion, the second security code 604 is deleted from the volatile memory 240. This is advantageous as it ensures that dose records in the medication dose history can no longer be decrypted by accessing the memory 241 of the apparatus 2.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about-4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A first device storing a computer code that when executed by the first device causes the first device to:
receive a first security code unique to a second device by retrieving through a first wireless communication technology, the first security code from a label printed on or attached on a housing of the second device, wherein the second device is configured to record information concerning a use of a medicament delivery device;
receive a packet broadcasted by the second device, the packet having (i) a second security code unique to the second device and stored on a memory of the second device, and (ii) an encrypted payload including a dose record, wherein the packet is received through a second wireless communication technology that is different from the first wireless communication technology;
generate a cryptographic key based on the first security code and the second security code, wherein the cryptographic key is unique to the second device and is generated for decrypting the encrypted payload; and
store the cryptographic key.

2. The first device according to claim 1, further configured to:
decrypt the encrypted payload using the cryptographic key to produce a decrypted dose record; and
store the decrypted dose record in a memory.

3. The first device according to claim 2, wherein the encrypted payload is a first encrypted payload, and the first device is further configured to:
in response to producing the decrypted dose record, determine whether any previous dose record is missing from the memory;
in response to determining that at least one previous dose record is missing from the memory, send a connection request to the second device;
receive from the second device a dose record packet having a second encrypted payload including the at least one previous dose record;
decrypt the encrypted payload of the dose record packet using the cryptographic key; and
store the at least one previous dose record in the memory.

4. The first device according to claim 1, wherein the cryptographic key is an initial cryptographic key, and
wherein the first device is further configured to transmit a new cryptographic key to the second device after the initial cryptographic key is generated,
wherein the new cryptographic key is encrypted using the initial cryptographic key.

5. The first device according to claim 1, further configured to generate the cryptographic key using at least one hash function in combination with the first security code and the second security code.

6. The first device according to claim 1, wherein the first device is a mobile device capable of wireless communication.

7. The method of claim 1, wherein the first wireless communication technology is a near-field communication (NFC) technology or an optical scanning technology.

8. A second device for recording information concerning a use of a medicament delivery device, the second device comprising:
a housing;
a transmitter configured to wirelessly broadcast data;
a label printed on or attached on the housing, and includes a first security code that is unique to the second device and is retrievable through a first wireless communication technology;
a memory configured to store a cryptographic key unique to the second device and a plurality of dose records; and
a processor configured to control the transmitter to broadcast a packet having (i) a second security code unique to and stored on the second device and (ii) an encrypted payload encrypted using the stored cryptographic key, the encrypted payload including a dose record, wherein the transmitter broadcasts the packet through a second wireless communication technology that is different from the first wireless communication technology,
wherein the first security code and the second security code are two factors of a two-factor authentication system for allowing generation of the cryptographic key.

9. The second device according to claim 8, wherein the second device is configured to:
detect a user input indicating that an injection process of the medicament delivery device is complete;
capture information representing a dosage dialed or delivered at the medicament delivery device;
generate the dose record from the captured information;
generate the encrypted payload including the dose record using the cryptographic key; and
broadcast the encrypted payload as part of the packet.

10. The second device according to claim 8, wherein the second device is further configured to:
receive a connection request from a first device, the connection request requesting a missing dose record; and
in response to receiving the connection request, control the transmitter to transmit the missing dose record to the first device.

11. The second device according to claim 8, wherein the cryptographic key is an initial cryptographic key, and
the second device is further configured to receive from a first device a new cryptographic key encrypted by the initial cryptographic key and to store the new cryptographic key.

12. The second device according to claim 8, further comprising:
a battery,
wherein the second device is further configured to:
delete the cryptographic key and the second security code from the volatile memory prior to depletion of the battery.

13. The second device according to claim 8, wherein the second device is a supplemental device provided with a part for coupling to the medicament delivery device.

14. The second device according to claim 8, wherein the second device is an integral part of the medicament delivery device.

15. A method executed by a monitoring system including a first device and a second device, the method comprising:
at the first device:

receiving a first security code unique to the second device by retrieving through a first wireless communication technology, the first security code from a label printed on or attached on the second device;

receiving a packet broadcasted by the second device, the packet having (i) a second security code unique to the second device and stored on a memory of the second device, and (ii) an encrypted payload including a dose record, wherein the packet is received through a second wireless communication technology that is different from the first wireless communication technology;

generating a cryptographic key based on the first security code and the second security code, wherein the cryptographic key is unique to the second device and is generated for decrypting the encrypted payload; and storing the cryptographic key.

16. The method according to claim 15, further comprising, at the second device:

detecting a user input indicating that an injection process of a medicament delivery device is complete;

capturing an image of a dosage dialled at the medicament delivery device representing the dose record;

generating the encrypted payload including the dose record using the cryptographic key of the second device;

generating the packet including the second security code and the encrypted payload; and broadcasting the packet.

17. The method according to claim 15, further comprising, at the first device:

decrypting the encrypted payload using the cryptographic key to produce a decrypted dose record; and storing the decrypted dose record in a memory.

18. The method according to claim 17, further comprising, at the first device:

in response to producing the decrypted dose record, determining whether any previous dose record is missing from the memory;

in response to determining that at least one previous dose record is missing, sending a connection request to the second device;

receiving from the second device a dose record packet having a second encrypted payload including the at least one previous dose record;

decrypting the second encrypted payload of the dose record packet using the cryptographic key; and storing the at least one previous dose record in the memory.

19. The method according to claim 15, wherein the cryptographic key is an initial cryptographic key, and the method further comprises:

after generating the initial cryptographic key at the first device, transmitting by the first device a new cryptographic key encrypted by the initial cryptographic key to the second device.

20. The method according to claim 15, further comprising, at the second device:

storing the cryptographic key and the second security code in a volatile memory; and deleting the cryptographic key and the second security code immediately prior to depletion of a battery of the second device.

* * * * *

UNITED STATES PATENT AND TRADEMARK OFFICE
CERTIFICATE OF CORRECTION

PATENT NO. : 12,362,054 B2  
APPLICATION NO. : 17/641190  
DATED : July 15, 2025  
INVENTOR(S) : Stefan Alt It is certified that error appears in the above-identified patent and that said Letters Patent is hereby corrected as shown below:

In the Claims

Column 28, Line 1, Claim 7, delete "method of" and insert --first device according to--

Signed and Sealed this  
Twenty-sixth Day of August, 2025

Coke Morgan Stewart  
*Acting Director of the United States Patent and Trademark Office*